US00PP31219P2

(12) United States Plant Patent
Hansen

(10) Patent No.: US PP31,219 P2
(45) Date of Patent: Dec. 10, 2019

(54) ***DELOSPERMA* PLANT NAMED 'SAUCY STRAWBERRY'**

(50) Latin Name: ***Delosperma* hybrid**
Varietal Denomination: Saucy Strawberry

(71) Applicant: Christopher M. Hansen, Zeeland, MI (US)

(72) Inventor: Christopher M. Hansen, Zeeland, MI (US)

( * ) Notice: Subject to any disclaimer, the term of this patent is extended or adjusted under 35 U.S.C. 154(b) by 0 days.

(21) Appl. No.: 16/350,514

(22) Filed: Nov. 26, 2018

(51) Int. Cl.
*A01H 5/02* (2018.01)

(52) U.S. Cl.
USPC ..... Plt./422

(58) Field of Classification Search
USPC ..... Plt./422
CPC ..... A01H 5/02
See application file for complete search history.

*Primary Examiner* — Annette H Para
(74) *Attorney, Agent, or Firm* — Penny J. Aguirre

(57) ABSTRACT

A new cultivar of *Delosperma* plant named 'Saucy Strawberry' that is characterized by its floriferous blooming habit, its cherry red flowers, its very compact and tight mounds of foliage that do not become long or leggy during the summer growing months, its strong re-blooming habit during the entire growing season and into late fall, its small plant size, its uniform rooting habit, and its uniform blooming period with other plants in the series.

2 Drawing Sheets

Botanical classification: *Delosperma* hybrid.
Variety denomination: 'Saucy Strawberry'.

CROSS REFERENCE TO RELATED APPLICATIONS

This application is co-pending with U.S. Plant Patent Applications filed for plants derived from the same breeding program that are entitled *Delosperma* Plant Named 'Coconut Crush' (U.S. Plant patent application Ser. No. 16/350,512), *Delosperma* Plant Named 'Fig Fusion' (U.S. Plant patent application Ser. No. 16/350,511), *Delosperma* Plant Named 'Pumpkin Perfection' (U.S. Plant patent application Ser. No. 16/350,509), *Delosperma* Plant Named 'Banana Blast' (U.S. Plant patent application Ser. No. 16/350,513), and *Delosperma* Plant Named 'Tangerine Tango' (U.S. Plant patent application Ser. No. 16/350,510).

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1).

BACKGROUND OF THE INVENTION

The present invention relates to a new and distinct cultivar of *Delosperma* plant, botanically known as *Delosperma cooperi* 'Saucy Strawberry' and will be referred to hereinafter by its cultivar name, 'Saucy Strawberry'. The new cultivar of *Delosperma* is a hardy herbaceous perennial grown for use as a landscape and container plant and is particularly suitable as a groundcover.

'Saucy Strawberry' arose from an ongoing breeding program by the Inventor in Hudsonville, Mich. The objective was to obtain a new series of *Delosperma* cultivars with more floriferous blooming habits, smaller and more compact and uniform plant habits, and blooming periods that are the same amongst all cultivars in the series when grown under the same conditions.

The Inventor made a controlled cross in July of 2014 in his test garden in Hudsonville, Mich. between an unnamed proprietary plant from the Inventor's breeding program, reference no. 275-3, as the female parent and pollen that was pooled from unnamed proprietary plants of *Delosperma* as the male parent. The exact male parent is therefore unknown. The Inventor selected 'Saucy Strawberry' as a single unique plant in June of 2016 from the resulting seedlings.

Asexual reproduction of the new cultivar was first accomplished by stem tip cuttings in April of 2015 in Hudsonville, Mich. Asexual propagation by stem tip cuttings has determined that the characteristics are stable and reproduced true to type in successive generations.

SUMMARY OF THE INVENTION

The following traits have been repeatedly observed and are determined to be the characteristics of the new cultivar. These attributes in combination distinguish 'Saucy Strawberry' as a unique cultivar of *Delosperma*.

1. 'Saucy Strawberry' exhibits a floriferous blooming habit with an average of 53 flowers per plant as a 10-week-old plant grown in a 1-quart container started from a 128-cell plug.
2. 'Saucy Strawberry' exhibits cherry red flowers.
3. 'Saucy Strawberry' exhibits very compact and tight mounds of foliage that do not become long or leggy during the summer growing months.
4. 'Saucy Strawberry' exhibits a strong re-blooming habit during the entire growing season and into late fall.

5. 'Saucy Strawberry' exhibits a height of 3.8 cm and 38 cm in width.
6. 'Saucy Strawberry' exhibits uniform rooting that occurs in just 10 days.
7. 'Saucy Strawberry' exhibits a uniform blooming period with other plants in the series.

The seed parent plant of 'Saucy Strawberry', no. 275-3, differs from 'Saucy Strawberry' in having a 30% taller plant habit, 65% less flowers and flowers that are duller and lighter red in color. 'Saucy Strawberry' can be most closely compared to the cultivars 'Jewel of Desert Garnet' (U.S. Plant Pat. No. 23,471) and 'WOWDRY1' (U.S. Plant Pat. No. 26,157). 'Jewel of Desert Garnet' is similar to 'Saucy Strawberry' in having red flowers and a flowering period of late spring through fall. 'Jewel of Desert Garnet' differs from 'Saucy Strawberry' in having less flowers; an average of 19 flowers per 10-week old plant, a taller plant height varying between 56 cm and 71 cm, flowers that are larger in size and a less floriferous re-bloom in fall. 'WOWDRY1' differs from 'Saucy Strawberry' in having larger flowers, less flowers; an average of 35 flowers per 10-week old plant, a taller plant height; an average of 10 cm, an average plant width of 91 cm and flowers that are magenta pink in color. 'Saucy Strawberry' can also be compared to cultivars with co-pending patent applications from the same breeding program that have the same blooming periods. 'Coconut Crush' differs from 'Saucy Strawberry' in having white flowers, 'Fig Fusion' differs from 'Saucy Strawberry' in having hot pink flowers, 'Pumpkin Perfection' differs from 'Saucy Strawberry' in having orange flowers, 'Banana Blast' differs from 'Saucy Strawberry' in having yellow flowers, and 'Tangerine Tango' differs from 'Saucy Strawberry' in having red-orange flowers.

BRIEF DESCRIPTION OF THE DRAWINGS

The following is a detailed description of the new cultivar as observed on 3-month-old plants of 'Saucy Strawberry' as grown outdoors in two-quart containers in Hudsonville, Mich.

The photograph in FIG. 1 provides a top view of 'Saucy Strawberry' in bloom.

Figure 1:
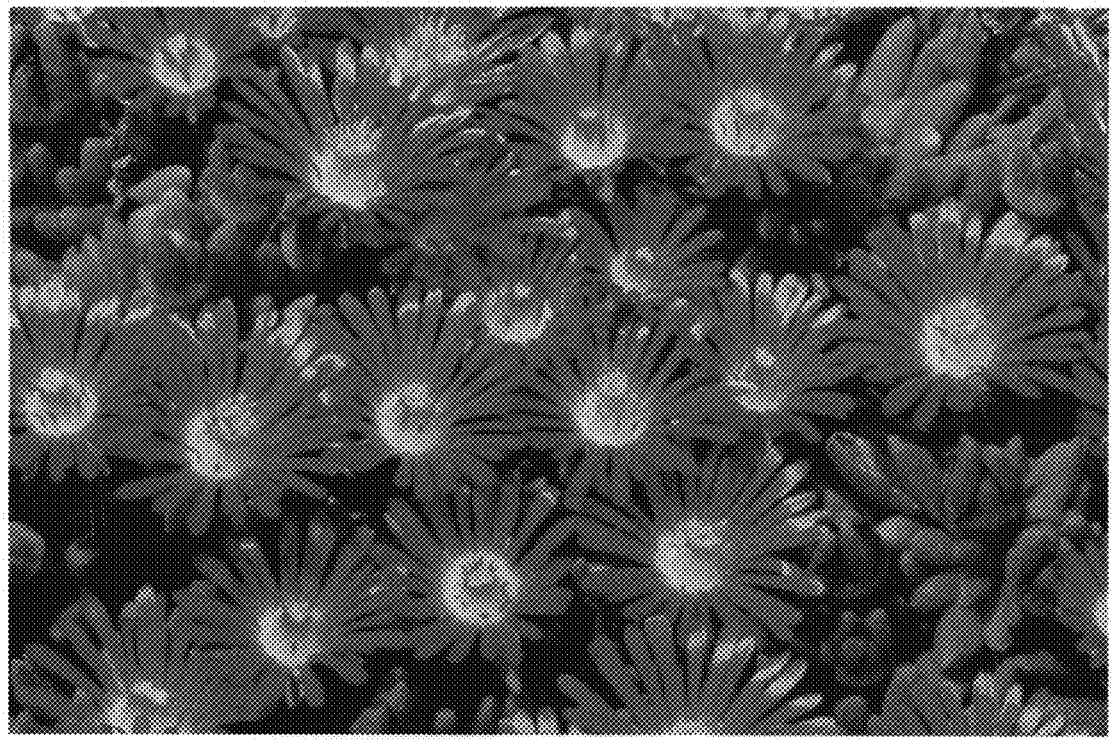
Figure 2:
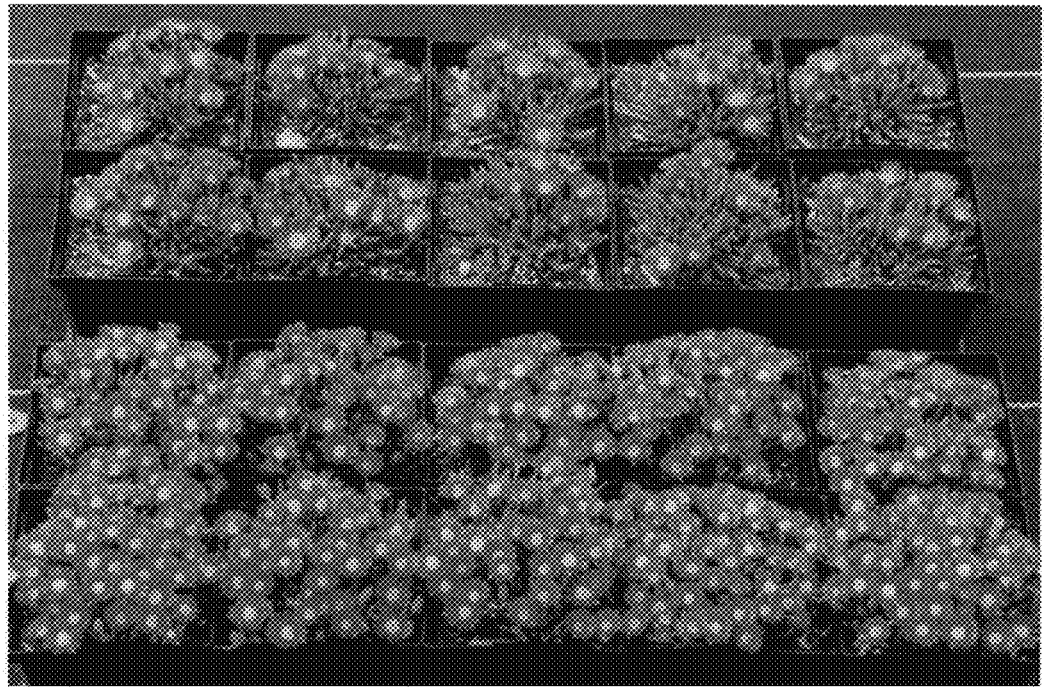

The photograph in FIG. 2 provides a comparison of 'Saucy Strawberry' (bottom) and 'Jewel of Desert Garnet' (top).

The colors in the photograph may differ slightly from the color values cited in the detailed botanical description, which accurately describe the colors of the new *Delosperma*.

DETAILED BOTANICAL DESCRIPTION

The following is a detailed description of 3-month-old plants of the new cultivar as grown in 9-cm containers outdoors in Hudsonville, Mich. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms heavily from June 1 through late July, then re-blooms through late October in Michigan.

*Plant type*.—Herbaceous perennial.

*Plant habit*.—Clumping, tightly mounded, compact ground cover.

*Height and spread*.—An average of 3.8 cm in height and about 38 cm in diameter in the landscape.

*Hardiness*.—At least in U.S.D.A. Zones 6 to 9.

*Diseases and pests*.—No susceptibility or resistance to diseases or pests has been observed.

*Root description*.—Fibrous roots, 199A in color.

*Root development*.—Cuttings root uniformly in 128-cell plugs in 6 weeks, 128-cell planted into a 9-cm pot or quart pot will finish and be in full bloom at 9 to 10 weeks after planting.

*Propagation*.—Stem tip cuttings.

*Growth habit*.—Moderate.

Stem description:

*Shape*.—Round.

*Stem color*.—Young stems; 145C, older stems 152A.

*Stem size*.—An average of 2 cm in length and 2 mm in diameter.

*Internode length*.—An average of 1 to 2 mm.

*Stem substance*.—Succulent, lower older stems become slightly woody.

*Stem surface*.—Young; moderately glossy and glabrous, mature is woody.

*Stem strength*.—Young; moderately strong, mature; strong.

*Branching habit*.—Freely and very densely branching, both basal and lateral, an average of 3 to 5 lateral branches per basal stem (lateral branches grow from basal stems), 20 basal stems per plant (growing just above the soil).

Foliage description:

*Leaf shape*.—Ligulate, oblong and narrow.

*Leaf substance*.—Succulent, thick.

*Leaf division*.—Simple.

*Leaf base*.—Cuneate.

*Leaf apex*.—Acute.

*Leaf venation*.—None visible.

*Leaf margins*.—Entire.

*Leaf arrangement*.—Opposite to whorled.

*Leaf surface* (*upper and lower surface*).—Densely pubescent with very short glandular hairs; too small to measure.

*Leaf color*.—Young and mature leaves; base 145C blending upward and becoming 146A.

*Leaf size*.—About 3 cm in length and 3 mm in width.

*Leaf quantity*.—Average of 16 per lateral branch.

*Leaf attachment*.—Sessile.

Inflorescence description:

*Inflorescence type*.—Flowers solitary, terminal.

*Flower number*.—Densely floriferous, quantity ranges, 3 to 4 per lateral stem.

*Flower fragrance*.—None.

*Flower aspect*.—Mostly held upright to slightly drooping as the plant spreads.

*Flower longevity*.—A few days, self-cleaning.

*Flower type*.—Single.

*Flower size*.—Average of 1.5 cm in diameter and 8 mm in depth.

*Flower buds*.—Broadly ovate to oblong in shape, an average of 1.5 cm in depth and 7 mm in diameter, color; 146A, surface is densely pubescent with minute hairs that match surface color.

*Calyx*.—Rotate in shape, average of 5 mm in depth and in diameter.

*Sepals*.—5, rotate, narrowly ovate in shape, margin entire, an average of 7 mm in length and 2 mm in width, acute apex, cuneate base, both surfaces glossy and densely covered with soft pubescence that matches the surface color, inner and outer surface is 143A in color, texture is thick and succulent.

*Petals*.—An average of 28 per flower, rotate and slightly curved downward, narrowly oblanceolate in shape, surface is smooth and glossy on both surfaces, margin entire, bluntly acute, base cuneate, an average of 5 mm in length and 1 mm in width, color; opening and fully open flowers upper surface; base NN155C, mid-section NN78A, blending out to tip 46A, opening and fully open flowers lower surface; NN78A.

*Petaloids*.—An average of 14 per flower, rotate, curved downward over petals and surrounding stamens, lanceolate in shape, moderately to highly glossy on both surfaces, margin entire, apex acute, base cuneate, an average of 3 mm in length and 0.75 mm in width, color upper and lower surface; NN78A.

*Peduncle*.—Average of 2 cm in length and 2 mm in diameter, held in multiple angles, surface is glossy, densely covered with minute pubescence matching surface color, color; 144B.

*Pedicel*.—None.

Reproductive organs:

*Pistils*.—5, an average of 1 mm in length, pistil, style and stigma are not distinguishable, triangular shaped, 142A in color, ovary is 142A in color.

*Stamens*.—Average 30, anthers; dorsifixed and narrowly oblong in shape, an average of 0.5 mm in diameter, 13A in color, filaments are up to 3 mm in length NN155D in color, pollen is high in quantity and 13A in color.

*Fruit*.—Fruit and seed production was not observed under the conditions tested.

It is claimed:

1. A new and distinct variety of *Delosperma* plant named 'Saucy Strawberry' as described and illustrated herein.

* * * * *